(12) United States Patent
Yamamoto et al.

(10) Patent No.: US 6,471,839 B1
(45) Date of Patent: Oct. 29, 2002

(54) BIOSENSOR

(75) Inventors: Tomohiro Yamamoto; Toshihiko Yoshioka; Shiro Nankai, all of Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/572,797

(22) Filed: May 17, 2000

(30) Foreign Application Priority Data

May 20, 1999 (JP) ............................................ 11-140672

(51) Int. Cl.[7] ............................................ G01N 27/327
(52) U.S. Cl. ................................ 204/403.06; 204/403.1
(58) Field of Search ........................... 204/403, 403.06, 204/403.1

(56) References Cited

U.S. PATENT DOCUMENTS

| | | | | |
|---|---|---|---|---|
| 5,382,346 A | * | 1/1995 | Uenoyama et al. | 204/403 |
| 5,385,846 A | * | 1/1995 | Kuhn et al. | 205/777.5 |
| 5,683,562 A | * | 11/1997 | Schaffar et al. | 204/403 |
| 5,707,502 A | * | 1/1998 | McCaffrey et al. | 204/403 |
| 5,762,770 A | * | 6/1998 | Pritchard et al. | 204/403 |
| 6,117,289 A | * | 9/2000 | Yamamoto et al. | 204/403 |

FOREIGN PATENT DOCUMENTS

| | | |
|---|---|---|
| JP | 01114747 A | 5/1989 |
| JP | 02062952 A | 3/1990 |

\* cited by examiner

*Primary Examiner*—T. Tung
*Assistant Examiner*—Alex Noguerola
(74) *Attorney, Agent, or Firm*—Akin, Gump, Strauss, Hauer & Feld, L.L.P.

(57) ABSTRACT

The present invention provides a biosensor which enables quick measurement and is excellent in storage characteristic. This biosensor comprises an electrically insulating base plate on which an electrode system having at least a measuring electrode and a counter electrode is formed, a cover member which is integrated to the base plate so as to form a sample solution supply path for supplying a sample solution to the electrode system between the cover member and the base plate, and a carrier composed of fiber supporting a reagent containing at least an oxidoreductase, and the carrier is placed in the sample solution supply path. Preferably, the carrier is constituted at least of two carrier pieces and each carrier piece supports a different reagent.

10 Claims, 8 Drawing Sheets

FIG. 9
(a) 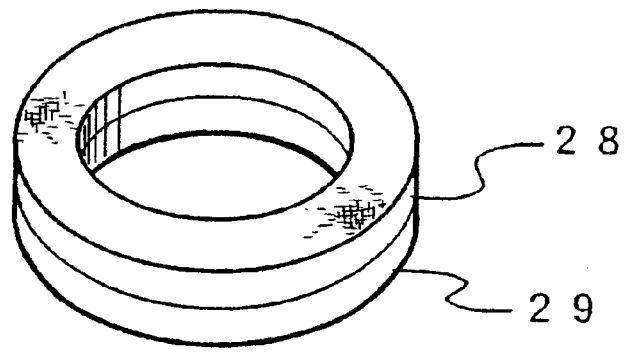
(b) 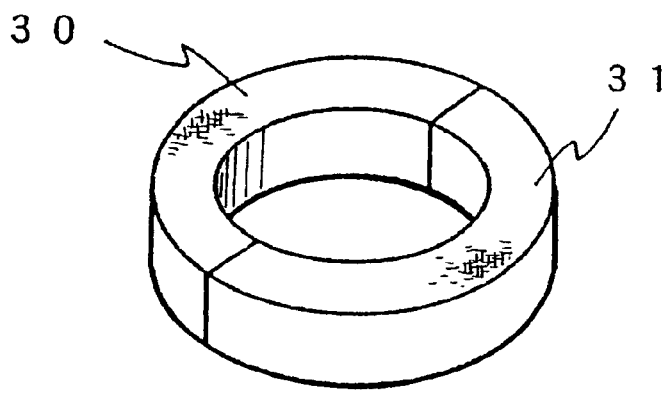
(c) 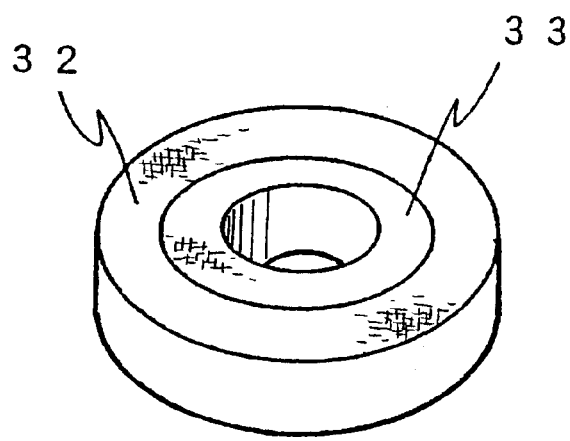

BIOSENSOR

BACKGROUND OF THE INVENTION

The present invention relates to a biosensor simply enabling rapid and high accuracy quantification of a measuring subject in a sample.

A biosensor has conventionally been proposed in the Japanese Laid-Open Patent Publication Hei 2-062952 as a system for simplified quantification of a specific component in a sample without diluting or agitating a sample solution.

This biosensor is completed by first forming an electrode system comprising a measuring electrode, a counter electrode and a reference electrode on an electrically insulating base plate by using a screen printing method or the like, and then forming an enzyme reaction layer comprising a hydrophilic polymer, an oxidoreductase and an electron mediator. If occasion demands, a buffer is added to this enzyme reaction layer.

Upon dropping a sample solution containing a substrate on the enzyme reaction layer thus formed, dissolution of the enzyme reaction layer takes place, which in turn triggers reaction between the enzyme and the substrate, causing a reduction of the electron mediator. Upon completion of the enzyme reaction, this reduced electron mediator is oxidized electrochemically. The concentration of the substrate in the sample solution can be determined by reading the oxidation current occurring in this procedure.

This biosensor can be used theoretically for measurements of various materials if an appropriate enzyme corresponding to the substrate of a target material is selected. For example, the use of glucose oxidase as the oxidoreductase can yield a biosensor for measurement of blood glucose level. This sensor is widely applied practically as a glucose sensor. The use of cholesterol oxidase as the oxidoreductase can yield a biosensor for measurement of serum cholesterol.

Serum cholesterol level which serves as diagnostic standard at various medical institutions is a sum of serum cholesterol and cholesterol ester concentrations. Since cholesterol ester cannot serve as a substrate for oxidation by cholesterol oxidase, a biosensor in which cholesterol oxidase is contained in a reaction layer cannot measure serum cholesterol level as diagnostic standard.

Therefore, a process for changing cholesterol ester into cholesterol is required. Cholesterol esterase is known as an enzyme for catalyzing this process. Inclusion of this cholesterol oxidase together with cholesterol oxidase in the enzyme reaction layer constitutes a biosensor for measurement of the total cholesterol concentration in serum.

The enzyme reaction layer of the biosensor having such constitution is formed by dropping a mixed aqueous solution containing an oxidoreductase, an electron mediator and the like onto the above-mentioned electrode system and drying the dropped solution. Such a procedure causes a problem that when the amount of reagents is large, the reaction layer is not dissolved quickly in dropping of the sample solution onto the reaction layer, and a long period of time is required for the measurement.

Particularly, in the sensor for measurement of the total cholesterol concentration in serum as described above, two kinds in total of enzymes, cholesterol oxidase and cholesterol esterase have to be contained in the enzyme reaction layer. Therefore, the amount of contained reagents increases significantly, so that a longer period of time is necessary for dissolution of the enzyme reaction layer after dropping of the sample solution, giving no quick measurement.

When the reagents such as an oxidoreductase and an electron mediator are contained in the enzyme reaction layer in such a condition that they are mixed with each other, the reagents may be degraded. Particularly, in the case of a long-period storage at high temperature, problems regarding deterioration of sensor response occur such as observation of large current value even if the substrate for the enzyme reaction is not contained in the sample solution.

BRIEF SUMMARY OF THE INVENTION

In view of the above-described drawbacks, an object of the present invention is to provide a biosensor which enables quick measurement by enhancing dissolution of reagents.

Another object of the present invention is to provide a biosensor which maintains excellent response characteristic even after a long-period storage.

A biosensor in accordance with the present invention comprises an electrically insulating base plate, an electrode system having at least a measuring electrode and a counter electrode formed on the base plate, a cover member which is integrated to the base plate so as to form a sample solution supply path for supplying a sample solution to the electrode system between the cover member and the base plate, and a carrier composed of fiber supporting a reagent containing at least an oxidoreductase, wherein the carrier is placed in the sample solution supply path.

Another biosensor in accordance with the present invention comprises an electrically insulating base plate, an electrode system having at least a measuring electrode and a counter electrode formed on the base plate, and a carrier composed of fiber supporting a reagent containing at least an oxidoreductase, wherein the carrier is fixed in the vicinity of the electrode system by an adhesive.

It is preferable that the above-described carrier is constituted at least of two carrier pieces and each carrier piece supports a different reagent.

BRIEF DESCRIPTION OF THE SEVERAL VIEWS OF THE DRAWING

FIG. 9 is a perspective view showing a constitution example of the carrier pieces of the biosensor of the present invention.

DETAILED DESCRIPTION OF THE INVENTION

Figure 1:
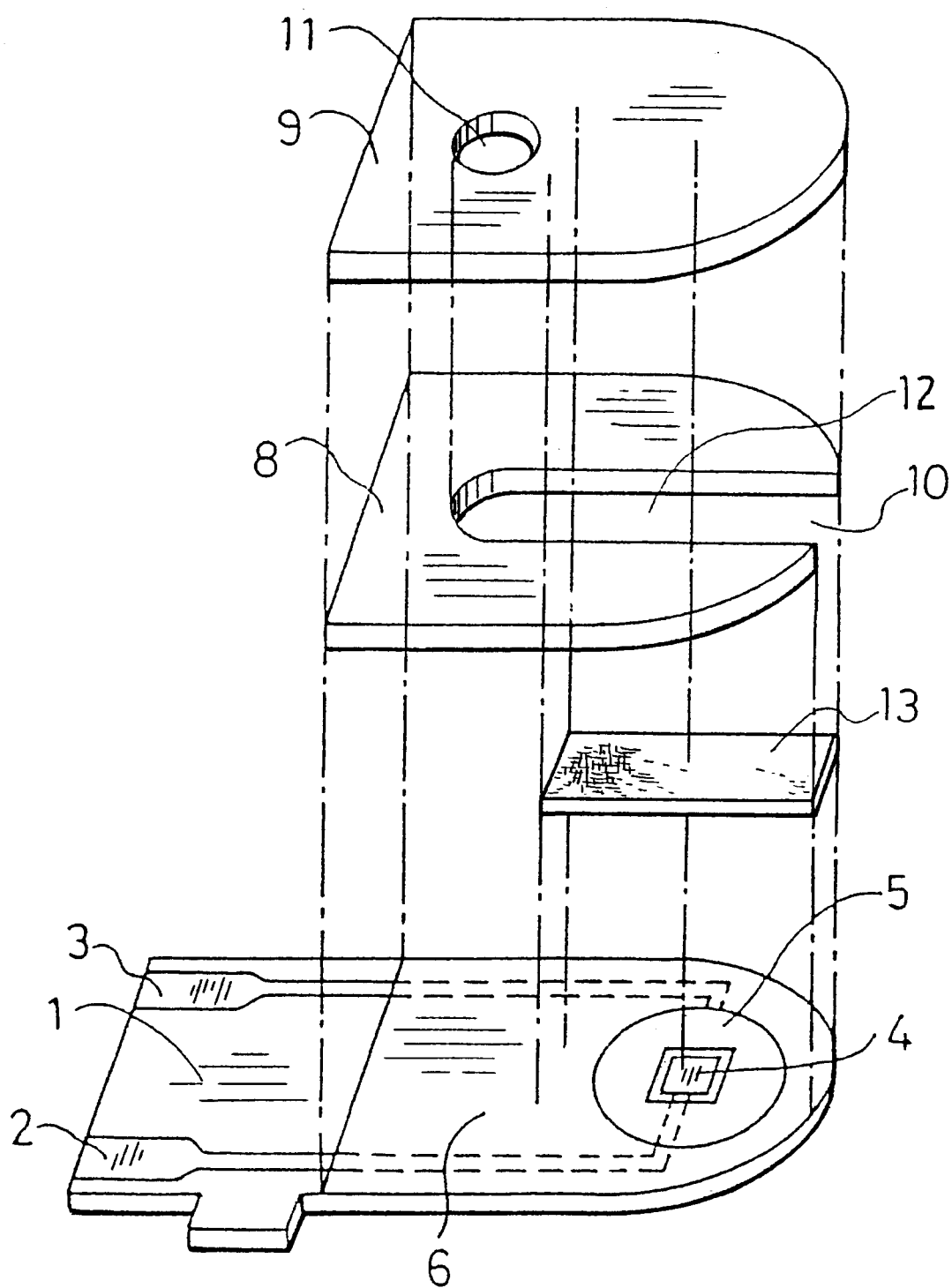
FIG. 1 is an exploded perspective view of a biosensor according to one example of the present invention from which a reaction layer is removed.

In the biosensor according to the present invention, a reagent such as an oxidoreductase or the like is supported on the surface of fiber constituting a carrier in such a condition that the reagent is dispersed onto the surface thereof. This constitution allows the reagent to get a wider contact surface area with a sample solution, improving the dissolution of the reagent into the sample solution.

For dispersing and supporting the reagent on the surface of the carrier as described above, the concentration of a reagent solution to be dropped onto the carrier may advantageously be controlled appropriately.

It is preferable that the carrier itself is inactive to the enzyme reaction and electrochemical reaction occurring in the biosensor, and a sheet made by laminating a cellulose fiber, a glass fiber or a polymeric compound fiber into a fleece or felt form is suitably used.

As the carrier, it is preferable to select one having a void ratio sufficient for quick permeation of the sample solution into the carrier when the sample solution is introduced to the sensor. For example, when filter paper composed of glass fiber is used as the carrier, its void ratio may be advantageously about 70 to 95%. As described later, when the carrier is fitted into a sample solution supply path of the biosensor, it is preferable that the carrier has some elasticity.

In another biosensor according to the present invention, a plurality of carriers are prepared, an oxidoreductase, an electron mediator and the like are supported on separate carriers, and they are separately contained in the biosensor. By this constitution, the dissolution of the reagent into the sample solution is improved, and the degradation of the reagent during storage can be controlled.

Regarding the positioning of the carrier in the biosensor, various changes are possible. In one embodiment, a carrier is fitted into the sample solution supply path of the cover member. In another embodiment, a carrier is fixed with an adhesive onto the surface exposed to the sample solution supply path of the cover member, or in the vicinity of the electrode system on the base plate.

For fitting the carrier into the sample solution supply path of the cover member, the carrier is molded into the same form as that of the sample solution supply path of the cover member and this is then placed into the sample solution supply path to be fixed to the cover member. By use of this method, the sensor fabrication process can be simplified, and the productivity can be improved. When a plurality of carriers are used, carriers molded into sizes smaller than that of the sample solution supply path of the cover member are prepared, and the respective carriers thus obtained may be combined appropriately to be fitted into the sample solution supply path.

For example, carriers having the same width as and smaller length than that of the sample solution supply path may be placed into the sample solution supply path sequentially from the sample solution flow-in side so that the sample solution can permeate each of the carriers sequentially, or rectangular carries having the same length as and smaller width than that of the sample solution supply path may be placed in parallel along the flow of the sample solution. Particularly, the latter layout is preferable since the sample solution quickly permeates the carriers to dissolve reagents, and uniform mixing of the dissolved reagents is facilitated.

Further, a plurality of carriers having smaller thickness may be prepared to be molded into the same form as that of the sample solution supply path of the cover member, and the molded carriers may be laminated to be fitted in the sample solution supply path.

In this case, it is preferable to divide carriers supporting different reagents into several pieces and to place these carriers in such a manner that the carriers supporting different reagents are adjacent to each other, because the reagents dissolved in the sample solution can be easily mixed.

When the carrier is fixed to the sensor using an adhesive, the carrier is fixed to a part which is away from the electrode system so that the adhesive and the carrier should not exert adverse influence on the electrode reaction.

As the adhesive, it is preferable to use adhesives having such high viscosity as to prevent permeation into the carrier under the environment of sensor production, for example, cellulose-based adhesives or woodworking adhesives such as the adhesive commercially available under the trade name of Cemedine C from Cemedine Co., Ltd.

When the carrier is fixed to the sensor by using such an adhesive, it is possible to prevent disturbance of electrode response which is caused when the carrier is swollen by the permeation of the sample solution and thereby moves to come in contact with the electrode system. When the plurality of carriers are used, these carriers may be placed so that they are separated from each other at certain distances.

Further, in a sensor having no cover member in which only an electrode system and a reaction layer are formed on a substrate, various forms of carries can be used. However, it is preferable that the carrier is fixed at a place as close to the electrode system as possible. For example, carriers in the form of a donut having the internal diameter larger than the outer diameter of the electrode system may be advantageously used. When reagents are separately supported on the carriers, different reagents are supported on a carrier 28 and a carrier 29 and the carriers are laminated in vertical direction to be fixed, as shown in FIG. 9(*a*). Further, a carrier 30 and a carrier 31 obtained by dividing the carrier in the form of a donut into equal halves along longitudinal direction thereof may be used as shown in FIG. 9(*b*), and a carrier 32 and a carrier 33 having different internal diameters may be used as shown in FIG. 9(*c*).

As the oxidoreductase to be supported on the carrier, various compounds can be used. For example, glucose oxidase, lactate oxidase, cholesterol oxidase, and the like are listed. When serum cholesterol level is measured, cholesterol oxidase and an enzyme having a cholesterol ester hydrolyzing activity are used. As the enzyme having a cholesterol ester hydrolyzing activity, cholesterol esterase, lipoprotein lipase and the like are listed. Particularly, cholesterol esterase is advantageous since it can convert cholesterol ester into cholesterol quickly by using a suitable surfactant.

When the enzyme having a cholesterol ester hydrolyzing activity is used as the oxidoreductase, it is preferable that a surfactant having the effect of improving the activity of this enzyme is contained in the reagent to be supported on the carrier, since the time required for the enzymatic reaction can be reduced. For example, as the surfactant for improving the activity of cholesterol esterase, it is possible to use n-octyl-β-D-thioglucoside, polyethylene glycol monododecyl ether, sodium cholate, dodecyl-β-maltoside, sucrose monolaurate, sodium deoxycholate, sodium taurodeoxycholate, N,N-bis(3-D-gluconeamidopropyl)

choleamide, N,N-bis(3-D-gluconeamidopropyl) deoxycholeamide, polyoxyethylene-p-t-octyl phenyl ether and the like.

Among these surfactants, when the surtactant which is a liquid having a high viscosity at ordinary temperature and does not disturb the enzyme reaction is used for the adhesive to fix the carrier, it is possible to obtain a merit that introduction of the sample solution into the sensor is facilitated in addition to the effect of improving the activity of the enzyme.

As the surfactant for this purpose, polyethylene glycol monododecyl ether, polyoxyethylene-p-t-octyl phenyl ether and the like are listed.

If the electrode system of the biosensor is formed by using an electrochemically stable metal such as platinum and the like, the obtained oxidation current value is free from an error. However, since such metal is expensive, the electrode system of a disposable sensor is prepared by forming a silver electrode by using a silver paste and the like and subsequently coating it with a carbon paste.

However, when the surfactant is contained in the sample solution, the sample solution permeates between carbon particles by the action of the surfactant. As a result, the activity of the carbon electrode may decrease, and the sample solution comes in contact with the silver electrode. Thus, when a voltage is applied on a measuring electrode under such condition, the silver electrode causes an oxidation reaction, so that a positive error may be included in the measured current value.

For suppressing such a phenomenon, there is a method that the surface of the electrode system is coated with a hydrophilic polymer. This hydrophilic polymer forms a viscose layer upon introduction of the sample solution, suppressing the contact of the sample solution with the electrode.

Examples of such hydrophilic polymer include carboxymethylcellulose, polyvinylpyrrolidone, polyvinyl alcohol, ethylcellulose, hydroxypropylcellulose, gelatin, polyacrylic acid and salts thereof, starch and derivatives thereof, polymer of maleic anhydride and salts thereof polyacrylamide, methacrylate resin, poly 2-hydroxyethyl methacrylate and the like.

When a solution prepared by dissolving an amphiphatic substance such as lecithin in an organic solvent is dropped and dried to form an amphiphatic substance layer to cover the above-mentioned hydrophilic polymer layer, the introduction of the sample solution can be conducted smoothly. Examples of such amphiphatic substance include phospholipid such as lecithin.

When the electrode system of the biosensor is formed by platinum and the like, the concentration of a substrate can be measured by using a dissolved oxygen in the sample solution. However, when the electrode system is formed with silver and a carbon layer covering the silver, it is extremely difficult to measure the oxidation current value of hydrogen peroxide produced from the dissolved oxygen. Further, since there is only a small amount of dissolved oxygen, the accurate value cannot be obtained when the concentration of the substrate is high. Therefore, when the electrode system of the biosensor is formed with silver and the carbon layer covering the silver, an electron mediator is required to be contained in the reagent supported on the carrier.

As the electron mediator, arbitrary water-soluble compounds which can mediate electron transfer between the enzyme and the electrode such as ferricyanide ion, p-benzoquinone, phenazine methosulfate and ferrocene may be used.

The degradation of the above-described various reagents can be suppressed more efficiently when they are supported separately on the carriers rather than when they are mixed with each other on the carriers.

Particularly, when the electron mediator is supported on a different carrier from the carriers supporting enzymes, the effect of controlling the degradation of the enzyme is remarkable.

When the enzyme having a cholesterol ester hydrolyzing activity is contained in the reagent, the sensor response is improved if a surfactant having an action to improve the activity of this enzyme is allowed to be supported on the carrier supporting this enzyme.

It is also possible that not all of the above-described reagents are supported on the carriers and that a layer containing some of the reagents is formed at a different place from the carrier to be contained in the reaction system.

In measuring the oxidation current, a two-electrode system composed only of a measuring electrode and a counter electrode and a three-electrode system further comprising a reference electrode are applicable, and the three-electrode system can give more accurate measurement results.

In the following, the present invention will be described more specifically, referring to concrete examples.

FIG. 1 is an exploded perspective view of the biosensor according to one example of the present invention from which a reaction layer is removed.

Numeral 1 represents an electrically insulating base plate made of polyethylene terephthalate. On this base plate 1, leads 2 and 3, and the ground for an electrode system are formed by printing a silver paste using a screen printing method. On the base plate, an electrically conductive carbon paste containing a resin binder is further printed to form the electrode system containing a measuring electrode 4 and a counter electrode 5, and an electrically insulating paste is printed to form an electrically insulating layer 6, respectively. The measuring electrode 4 is connected to the lead 2, and the counter electrode 5 is connected to the lead 3, respectively. The electrically insulating layer 6 allows the areas of exposed portions of the measuring electrode 4 and the counter electrode 5 to be constant and covers the leads partially.

The electrically insulating base plate 1 on which the electrode system is thus formed, a cover 9 having an air vent 11, a spacer 8 and a carrier 13 supporting a reagent are adhered under the positional relation as shown by the dotted chain lines in FIG. 1 to form a biosensor.

In the biosensor having such constitution, between the base plate 1 and the cover 9, a space constituting a sample solution supply path is formed at the part of a slit 12 of the spacer 8, and the carrier 13 is placed in this space.

By a simple operation of bringing a sample solution into contact with an opening 10 forming a port of the sample solution supply path, the sample solution is introduced easily into the sensor.

Figure 2:
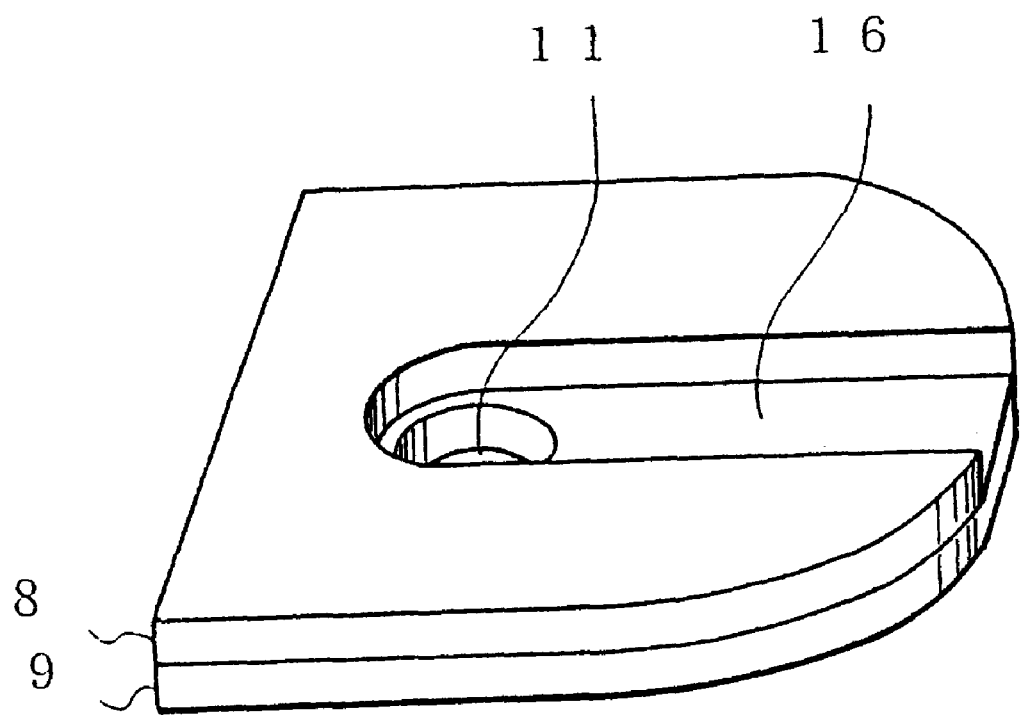
FIG. 2 is a perspective view of a cover member formed by integrating a cover and a spacer of the same biosensor, placed upside down against the view of FIG. 1.

FIG. 2 is a perspective view of a cover member formed by laying the spacer 8 on top of the cover 9, which is a reverse layout to the view of FIG. 1. By combining this cover member with the base plate, the space constituting the sample solution supply path is formed. Numeral 16 represents the cover side of a surface exposed to this space constituting the sample solution supply path.

Figure 3:
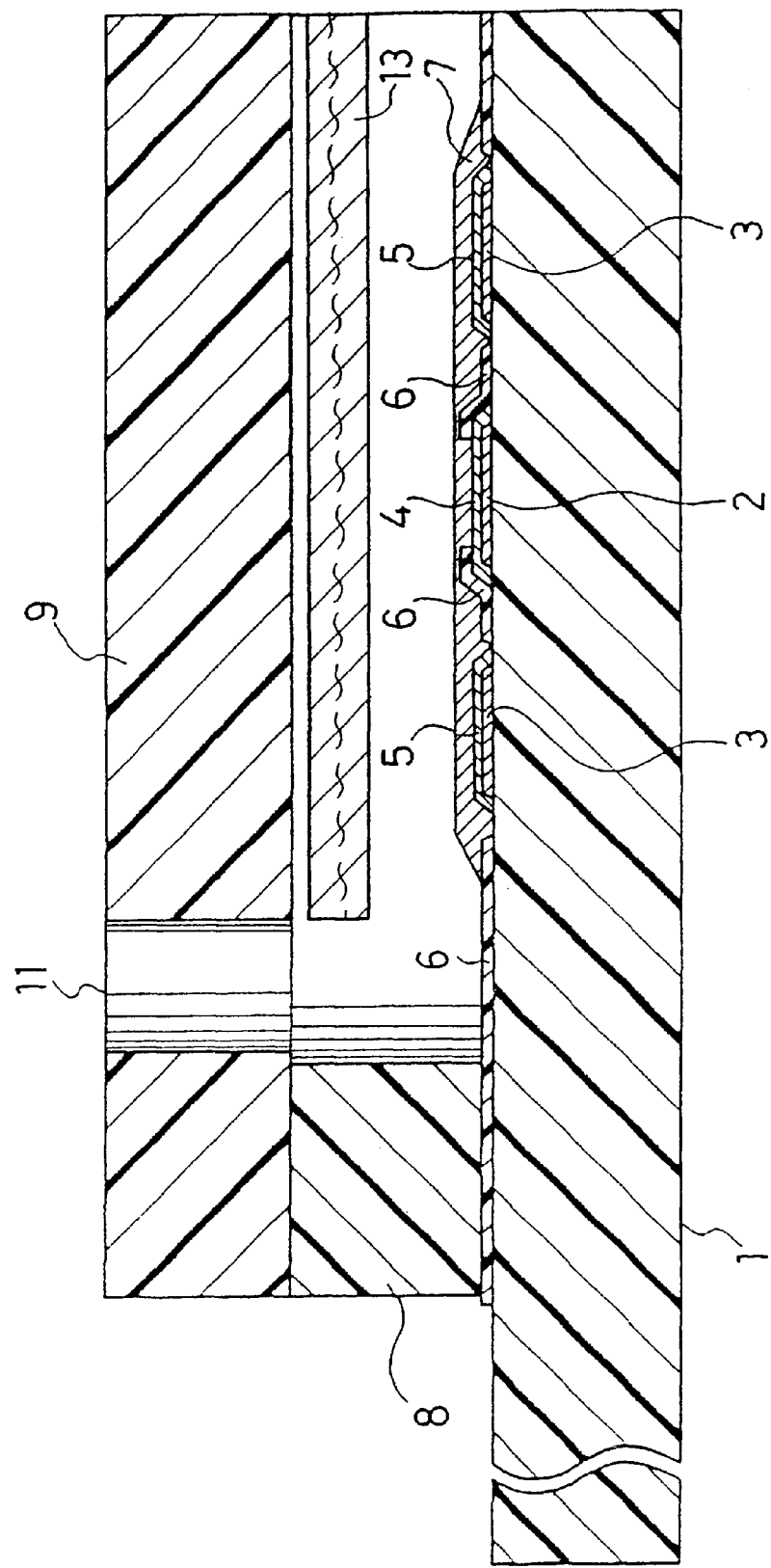
FIG. 3 is a longitudinal sectional view of the main parts of the same biosensor.

FIG. 3 is a longitudinal sectional view of the biosensor according to one example of the present invention. On the electrode system on the electrically insulating base plate 1, a hydrophilic polymer layer 7 is formed, and a lecithin layer 17 is formed so as to coat this layer 7. The carrier 13 supporting the reagent is placed so as to be fitted in the space constituting the sample supply path.

Figure 4:
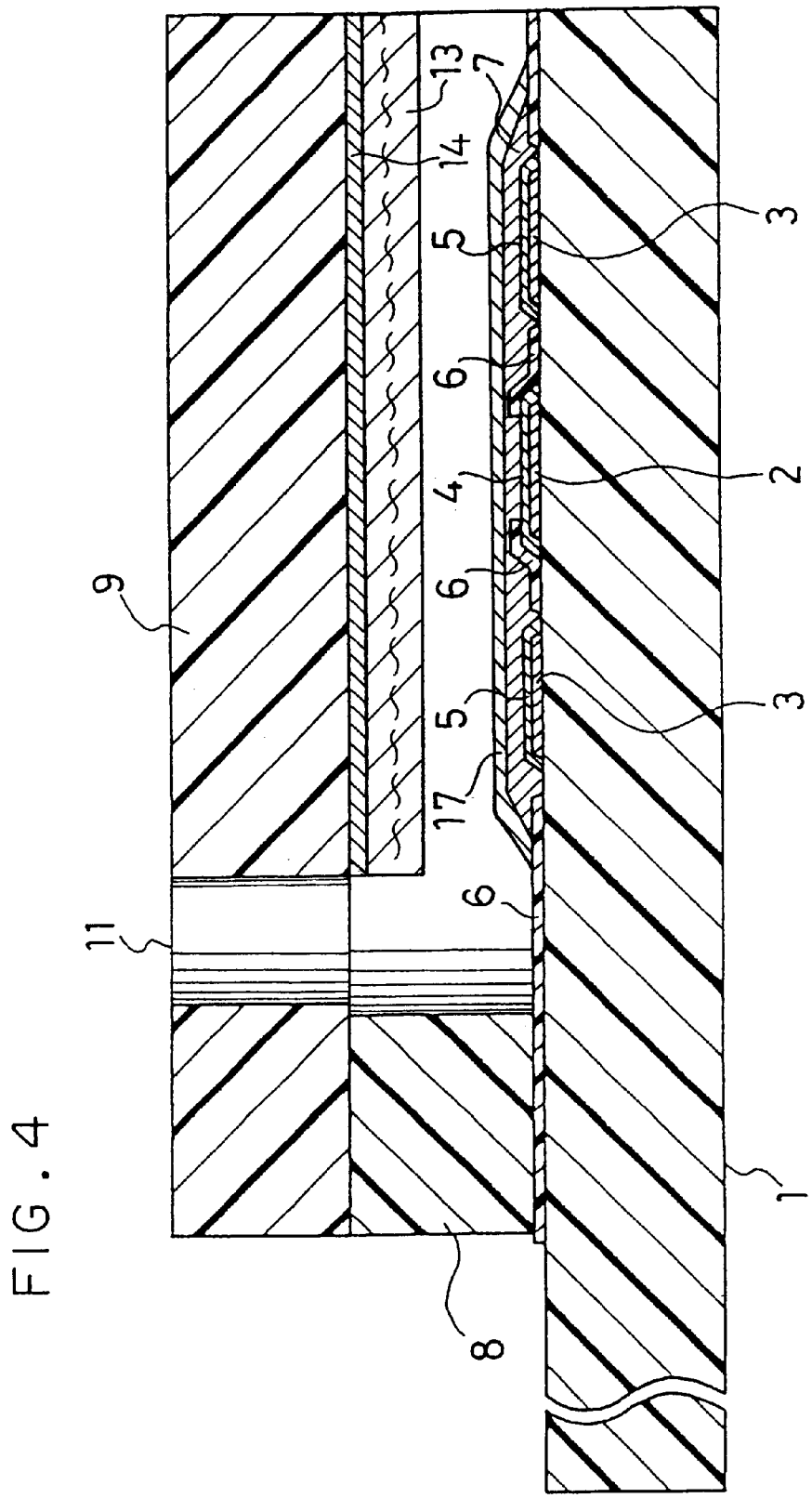
FIG. 4 is a longitudinal sectional view of the main parts of a biosensor of another example of the present invention.

FIG. 4 is a longitudinal sectional view of the biosensor of another example of the present invention. In the same manner as in FIG. 1, the electrode system is formed on the electrically insulating base plate 1, and the hydrophilic polymer layer 7 and the lecithin layer 17 are formed on this electrode system. Further, the carrier 13 supporting the reagent is fixed with an adhesive 14 onto the surface 16 of the cover side of the sample solution supply path.

Figure 5:
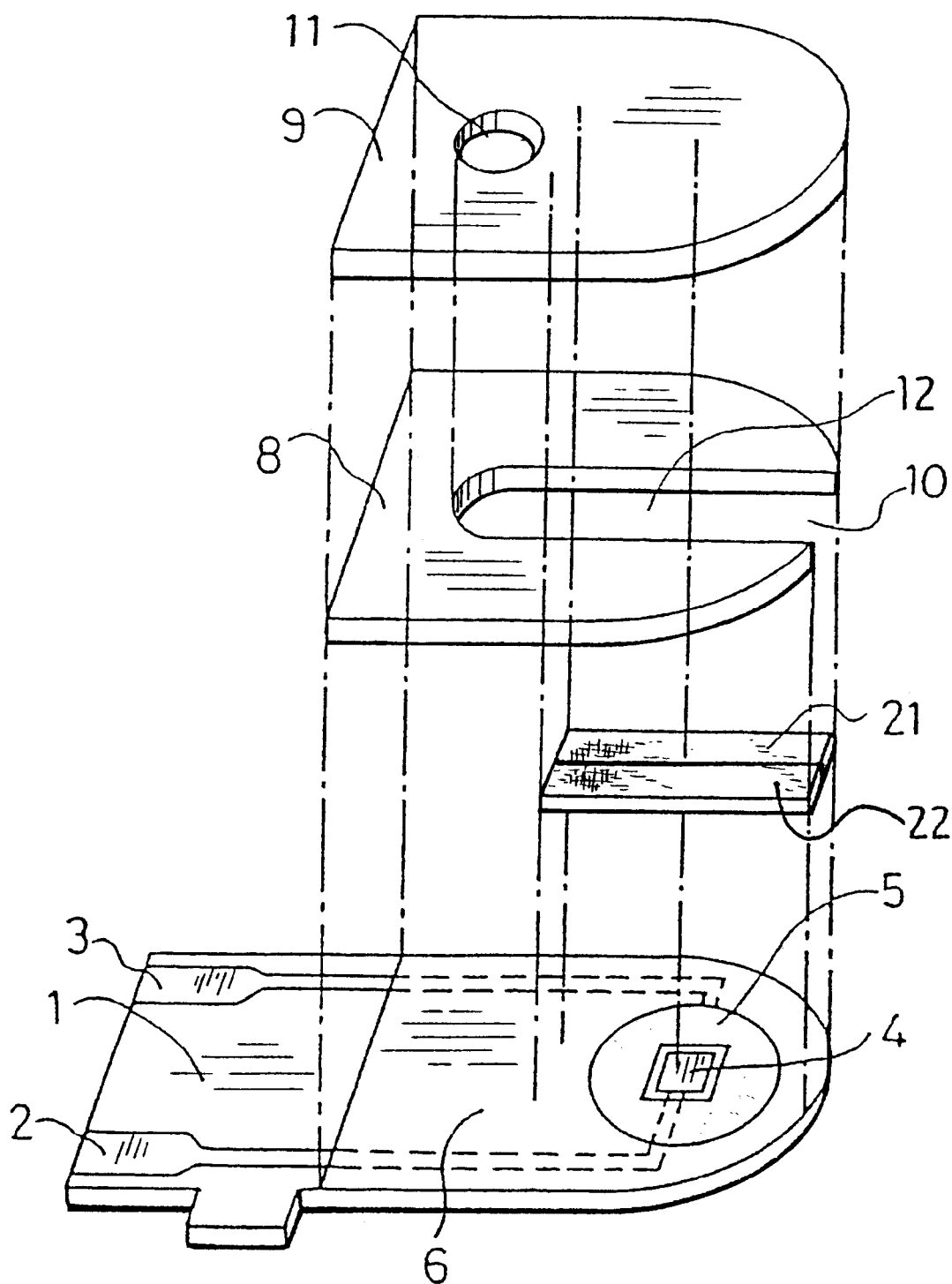
FIG. 5 is an exploded perspective view of a biosensor according to still another example of the present invention from which a reaction layer is removed.

FIG. 5 is an exploded perspective view of the biosensor according to another example of the present invention from which the reaction layer is removed. The electrically insulating base place 1 on which the electrode system is formed, the cover 9 having the air vent 11, the spacer 8 and carrier pieces 21 and 22 supporting different reagents are adhered under the positional relation as shown by the dotted chain lines in FIG. 5, in the same manner as in FIG. 1, to form the biosensor.

EXAMPLE 1

In this example, a biosensor having the constitution in FIG. 3 was manufactured as described below.

First, on the electrode system on the base plate 1 in FIG. 1, a 0.5 wt % aqueous solution of sodium salt of carboxymethylcellose (hereinafter abbreviated to CMC) which is a hydrophilic polymer was dropped and dried in a hot air drier for 10 minutes at 50° C. to form a CMC layer 7. Then, 3 µl of a 0.5% toluene solution of lecithin was dropped to cover this CMC layer 7, and dried to form a lecithin layer 17.

Then, a cover made of an acrylic resin as shown in FIG. 2 was prepared. The length from the opening 10 to the end of the air vent 11 was 4.5 mm, the width of the slit 12 was 2.0 mm, and the depth of the slit was 0.3 mm. Felt composed of glass fiber having a thickness of 0.2 mm (hereinafter referred to as glass filter) was cut into 2×4.5 mm. Then, this glass filter was fitted into the slit 12 of the cover member to be fixed.

To this glass filter was dropped 5 µl of a mixed solution prepared by dissolving, into water, cholesterol oxidase (hereinafter referred to as ChOD), cholesterol esterase (hereinafter referred to as ChE), potassium ferricyanide as the electron mediator, and polyoxyethylene-p-t-octyl phenyl ether (hereinafter referred to as TritonX-100) as the surfactant having an action to activate the reaction of the cholesterol esterase, and dried in a hot air drier for 15 minutes at 50° C. to form a carrier 13 supporting reagents.

This cover member and the base plate 1 were adhered under the positional relation as shown by the dotted chain lines in FIG. 1 to form a biosensor.

To the biosensor thus manufactured was supplied 3 µl of a sample solution via the opening 10 of the sample solution supply path. Various solutions were used as the sample solution, and they were prepared by diluting a commercially available standard serum with physiological saline to change the concentration of the cholesterol contained. Three minutes after supply of the sample solution, a pulse voltage of +0.5 V was applied to the measuring electrode in the anodic direction based on the counter electrode, and 5 minutes after this voltage application, the current value flowing between the measuring electrode and the counter electrode was measured.

As a result, the current value increased along with the increase in the total cholesterol concentration in serum, showing excellent linearity between them.

EXAMPLE 2

In this example, a biosensor having the constitution shown in FIG. 4 was manufactured as described below.

In the same manner as in Example 1, a CMC layer 7 and a lecithin layer 17 were sequentially formed on the electrode system on the base plate 1 in FIG. 1.

Then, the same glass fiber as in Example 1 was cut into 2×4.5 mm. Then, a woodworking adhesive as the adhesive 14 was applied to a surface 16 of the cover side of the sample solution supply path, to which the glass filer was adhered and fixed.

To this glass filter was dropped 5 µl of a mixed aqueous solution prepared by dissolving the same reagents as in Example 1, and dried in a hot air drier for 15 minutes at 50° C. to form a carrier 13 supporting reagents.

A biosensor was manufactured, and the current response to the same sample solutions was measured, in the same manner as in Example 1.

Figure 10:
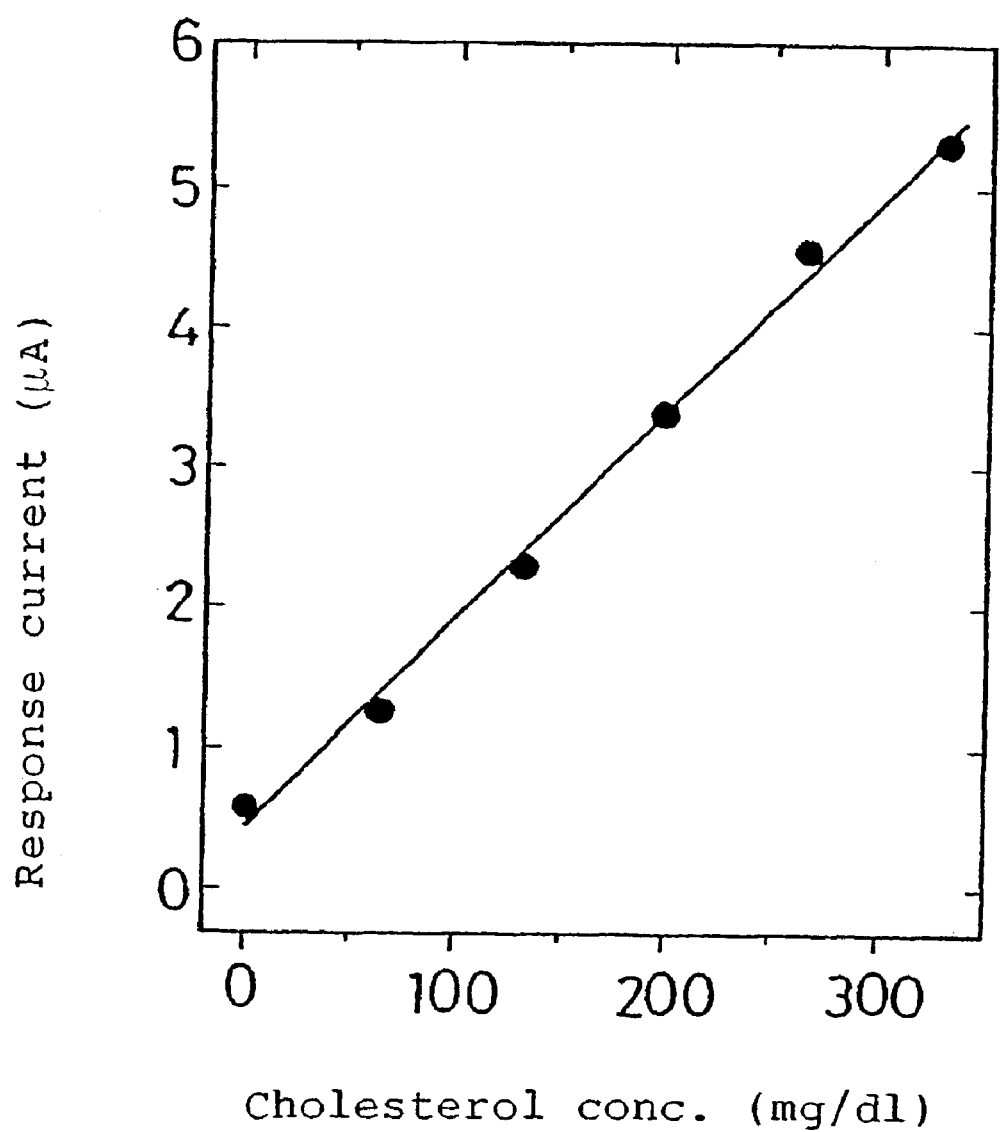
FIG. 10 is a graph showing the response characteristic of a biosensor according to one example of the present invention.

As a result, excellent response value depending on the total cholesterol concentration in serum was obtained as shown in FIG. 10.

EXAMPLE 3

In this example, a biosensor having the constitution shown in FIG. 4 was manufactured as described below.

In the same manner as in Example 1, a CMC layer 7 and a lecithin layer 17 were sequentially formed on the electrode system on the base plate 1 in FIG. 1. Then, onto a surface 16 of the cover side of the sample solution supply path, an ethanol solution of a surfactant TritonX-100 was dropped, and ethanol was vaporized to form a TritonX-100 layer 14 in the form of paste having function of an adhesive. Thereafter, felt (hereinafter referred to as cellulose filter) composed of cellulose fiber cut into 2×4.5 mm was adhered and fixed on this layer 14. Since TritonX-100 has a high viscosity though it is liquid at normal temperature (about 25° C.), it did not permeate into the cellulose filter.

To this cellulose filter was dropped 5 µl of a mixed aqueous solution prepared by dissolving the same reagents as in Example 1, and dried in a hot air drier for 15 minutes at 50° C. to form a carrier 13 supporting reagents.

A biosensor was manufactured, and the current response to the same sample solutions was measured, in the same manner as in Example 1.

As a result, excellent response value depending on the total cholesterol concentration in serum was obtained. Further, owing the use of the surfactant for adhering the carrier, introduction of the sample solution was very easy.

EXAMPLE 4

In the same manner as in Example 1, a CMC layer 7 and a lecithin layer 17 were sequentially formed on the electrode system on the base plate 1 in FIG. 1.

Then, similar two glass filters having a thickness of 0.2 mm to those of Example 1 were prepared. On one glass filter, a 0.6 mol/l aqueous solution of potassium ferricyanide as the electron mediator was dropped and allowed to permeate uniformly. This was dried in a hot air drier at 50° C. for 15 minutes to allow potassium ferricyanide to be supported on the filter in an amount of 0.33 µmol per 1 $mm^2$. This filter was cut into 1×4.5 mm to obtain a carrier piece 21 containing potassium ferricyanide.

Then, on the other filter was dropped an aqueous solution containing 400 units/ml ChOD, 4,000 units/ml ChE and 6 wt % TritonX-100, and allowed to permeate uniformly. Then, this was dried in a hot air drier for 15 minutes at 50° C. to allow 0.22 units of ChOD, 2.2 units of ChE and 0.3 mg of TritonX-100 to be supported per 1 $mm^2$. This glass filter was cut into 1×4.5 mm to obtain a carrier piece 22 containing ChOD, ChE and TritonX-100.

Figure 6:
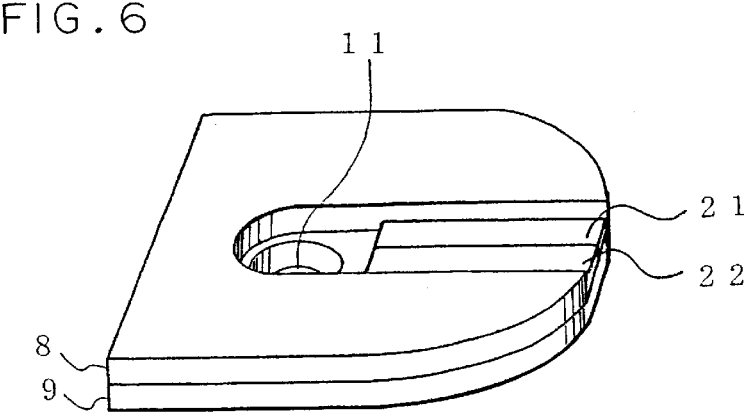
FIG. 6 is a perspective view of carrier pieces placed on the sample solution supply path of the cover member of the same biosensor.

The carrier pieces 21 and 22 were placed in a slit 12 of a cover member having the same form as in Example 1 as shown in FIG. 6 to be fixed. This cover member and the base plate 1 were adhered under the positional relation as shown by the dotted chain lines in FIG. 5 to form a biosensor. The current response value for the same sample solutions as in Example 1 was measured. As a result, excellent response value depending on the total cholesterol concentration in serum was obtained.

Then, a biosensor manufactured in the same manner was stored for 1 week at 50° C. Then, the current response value was measured in the same manner, and as a result, excellent response value depending on the total cholesterol concentration in serum was obtained. The response value (blank value) for a sample containing no substrate (sample only containing physiological saline) was close to that of the sensor immediately after the manufacture.

EXAMPLE 5

In the same manner as in Example 1, a CMC layer 7 and a lecithin layer 17 were sequentially formed on the electrode system on the base plate 1 in FIG. 1.

Then, similar three glass filters having a thickness of 0.2 mm to those of Example 1 were prepared.

One glass filter was allowed to support potassium ferricyanide in the same manner as in Example 1. However, the concentration of the potassium ferricyanide solution dropped was 0.9 mol/l, and the amount of supported potassium ferricyanide per 1 $mm^2$ of the glass filter was 0.5 $\mu$mol.

On the second glass filter, a 600 units/ml aqueous solution of ChOD was dropped and dried to allow 0.33 units ChOD to be supported per 1 $mm^2$ of the glass filter.

On the third glass filter, a mixed aqueous solution containing 6,000 units/ml ChE and 9 wt % TritonX-100 was dropped and dried to allow 3.3 units ChE and 0.45 mg TritonX-100 to be supported on the glass filter per 1 $mm^2$.

These three glass filters were cut into 0.66×4.5 mm to obtain a carrier piece 23 containing potassium ferricyanide, a carrier piece 24 containing ChOD, and a carrier piece 25 containing ChE and TritonX-100.

Figure 7:
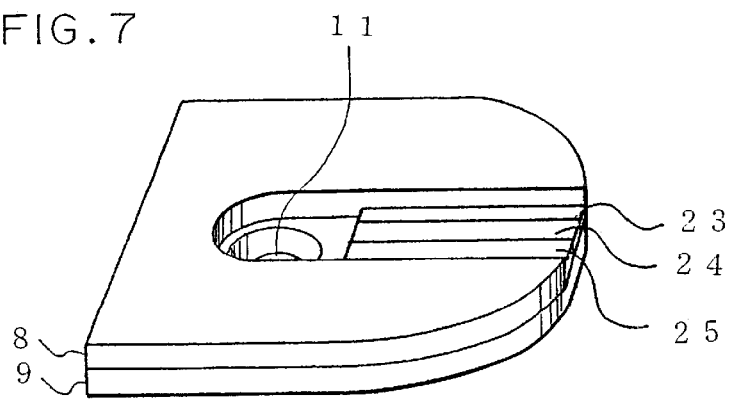
FIG. 7 is a perspective view of carrier pieces placed on the sample solution supply path of the cover member of a biosensor according to another example of the present invention.

Then, a woodworking adhesive commercially available under the trade name of Cemedine C from Cemedine Co., Ltd. was applied to a surface 16 of a cover member having the same form as in Example 1, and these carrier pieces were place and fixed as shown in FIG. 7.

Then, a biosensor was manufactured, and the current response values of the sensor immediately after the manufacture and after storage at 50° C. for 1 week were measured. in the same manner as in Example 4.

As a result, excellent response value depending on the total cholesterol concentration in serum was obtained in any of the sensor immediately after the manufacture and after storage. Further, the blank value of the sensor after storage was approximately the same as the blank value of the sensor immediately after the manufacture.

As described above, by supporting an electron mediator, ChOD, and a mixture of ChE and a surfactant on separate carriers, further excellent storage characteristic is obtained.

EXAMPLE 6

In the same manner as in Example 1, a CMC layer 7 and a-lecithin layer 17 were sequentially formed on the electrode system on the base plate 1 in FIG. 1.

Then, onto a surface 16 of the cover side of the sample solution supply path, an ethanol solution of a surfactant TritonX-100 was dropped, and ethanol was vaporized to form a TritonX-100 layer in the form of paste having function of an adhesive.

On the other hand, similar two glass filters having a thickness of 0.2 mm to those of Example 1 were prepared. One glass filter was allowed to support 0.33 $\mu$mol potassium ferricyanide per 1 $mm^2$ in the same manner as in Example 4. The other glass filter was allowed to support 0.22 units of ChOD, 2.2 units of ChE and 0.3 mg of TritonX-100 per 1 $mm^2$.

These two glass filters were each cut into three pieces of 0.33×4.5 mm to prepare carrier pieces 26 containing potassium ferricyanide, and carrier pieces 27 containing ChOD, ChE and TritinX-100.

Figure 8:
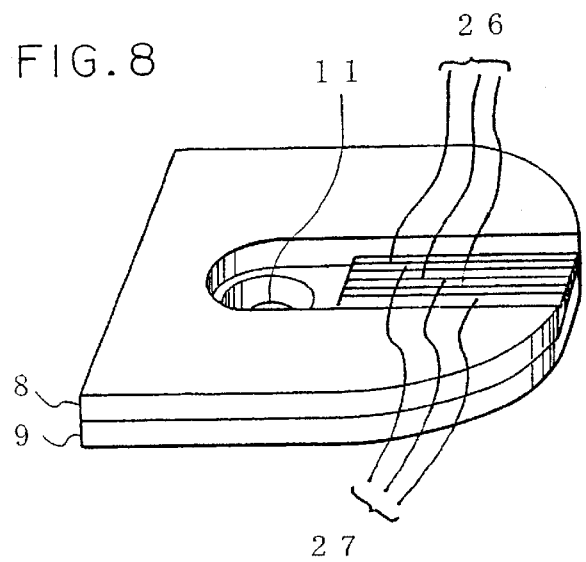
FIG. 8 is a perspective view of carrier pieces placed on the sample solution supply path of the cover member of a biosensor according to another example of the present invention.

Then, these carrier pieces 26 and carrier pieces 27 were placed alternately as shown in FIG. 8, and fixed on the TritonX-100 layer of the slit 12 of the cover member.

Then, a biosensor was manufactured in the same manner as in Example 4, and the current response values of the sensor immediately after the manufacture and after storage at 50° C. for 1 week were measured.

As a result, excellent response value depending on the total cholesterol concentration in serum was obtained in any of the sensor immediately after the manufacture and after storage.

As described above, by preparing a plurality of carrier pieces supporting different reagents and placing them alternately, the reagent degradation in storage can be suppressed, and the mixing of reagent components in permeation of the sample solution can be facilitated, so that the sensor response can be improved.

As described above, measurement of the concentration of a specific substance can be conducted quickly and at high accuracy, according to the present invention.

While the novel features of the invention are set forth particularly in the appended claims, the invention, both as to organization and content, will be better understood and appreciated, along with other objects and features thereof, from the following detailed description taken in conjunction with the drawings.

What is claimed is:

1. A biosensor comprising an electrically insulating base plate, an electrode system having at least a measuring electrode and a counter electrode formed on said base plate, a cover member which is integrated to said base plate so as to form a sample solution supply path for supplying a sample solution to said electrode system between said cover member and said base plate, and a carrier comprising at least two carrier pieces, each piece comprising a fiber supporting a reagent, a first piece supporting at least an oxidoreductase and at least a second piece supporting a different reagent, wherein said carrier is placed in said sample solution supply path, in the vicinity of, but not contacting, the electrode system.

2. The biosensor in accordance with claim 1, wherein said carrier is fixed in said sample solution supply path by an adhesive.

3. A biosensor comprising an electrically insulating base plate, an electrode system having at least a measuring electrode and a counter electrode formed on said base plate, a cover member which is integrated to said base plate so as to form a sample solution supply path for supplying a sample solution to said electrode system between said cover member and said base plate, and a carrier composed of fiber supporting a reagent containing at least an oxidoreductase, wherein said carrier is placed in said sample solution supply path and wherein said carrier is fixed in said sample solution supply path by an adhesive, further wherein said reagent contains at least cholesterol oxidase, cholesterol esterase and an electron mediator and said adhesive is a surfactant.

4. A biosensor comprising an electrically insulating base plate, an electrode system having at least a measuring electrode and a counter electrode formed on said base plate, a cover member which is integrated to said base plate so as to form a sample solution supply path for supplying a sample solution to said electrode system between said cover member and said base plate, and a carrier comprising at least two carrier pieces, each piece comprising a fiber supporting a reagent, a first piece supporting at least an oxidoreductase and at least a second piece supporting a different reagent, wherein said carrier is placed in said sample solution supply path, wherein said different reagent contains at least cholesterol oxidase, cholesterol esterase and an electron mediator, and the oxidoreductase and the electron mediator are supported on separate carrier pieces.

5. A biosensor comprising an electrically insulating base plate, an electrode system having at least a measuring electrode and a counter electrode formed on said base plate, a cover member which is integrated to said base plate so as to form a sample solution supply path for supplying a sample solution to said electrode system between said cover member and said base plate, and a carrier comprising at least two carrier pieces, each piece comprising a fiber supporting a reagent, a first piece supporting at least an oxidoreductase and at least a second piece supporting a different reagent, wherein said carrier is placed in said sample solution supply path, wherein said different reagent comprises at least cholesterol oxidase, cholesterol esterase, a surfactant and an electron mediator, and the carrier piece containing the cholesterol esterase contains the surfactant.

6. The biosensor in accordance with claim 5, wherein said reagent contains at least cholesterol oxidase, cholesterol esterase, a surfactant and an electron mediator, and wherein said electrode system comprises silver and a carbon layer covering the silver, and said electrode system is coated with a hydrophilic polymer.

7. A biosensor comprising an electrically insulating base plate, an electrode system having at least a measuring electrode and a counter electrode formed on said base plate, and a carrier composed of fiber supporting a reagent containing at least an oxidoreductase, the carrier comprising at least two carrier pieces, each carrier piece supporting a different reagent, wherein said carrier is fixed by an adhesive in the vicinity of, but not contacting, said electrode system.

8. A biosensor comprising an electrically insulating base plate, an electrode system having at least a measuring electrode and a counter electrode formed on said base plate, and a carrier composed of fiber supporting a reagent containing at least an oxidoreductase, wherein said carrier is fixed by an adhesive in the vicinity of said electrode system, wherein said reagent contains at least cholesterol oxidase, cholesterol esterase and an electron mediator, and said adhesive is a surfactant.

9. The biosensor in accordance with claim 8, wherein said electrode system comprises silver and a,carbon layer covering the silver, and said electrode system is coated with a hydrophilic polymer.

10. A biosensor comprising an electrically insulating base plate, an electrode system having at least a measuring electrode and a counter electrode formed on said base plate, and a carrier composed of fiber supporting a reagent containing at least an oxidoreductase, wherein said carrier is fixed by an adhesive in the vicinity of said electrode system, wherein said reagent contains at least cholesterol oxidase, cholesterol esterase and an electron mediator, and the oxidoreductase and the electron mediator are supported on separate carrier pieces.

* * * * *